United States Patent [19]

Ocain et al.

[11] Patent Number: 5,075,451
[45] Date of Patent: Dec. 24, 1991

[54] PYRROLIMIDAZOLONES USEFUL AS RENIN INHIBITORS

[75] Inventors: Timothy D. Ocain, Princeton, N.J.; David D. Deininger, Arlington, Mass.

[73] Assignee: American Home Products Corporation, New York, N.Y.

[21] Appl. No.: 614,363

[22] Filed: Nov. 16, 1990

Related U.S. Application Data

[62] Division of Ser. No. 490,810, Mar. 8, 1990, Pat. No. 5,023,338.

[51] Int. Cl.[5] .......................... C07D 235/00
[52] U.S. Cl. .................................. 548/302
[58] Field of Search ......................... 548/302

[56]  References Cited

U.S. PATENT DOCUMENTS 4,312,809 1/1982 Haugwitz ..................... 548/467
4,814,342 3/1989 Hoover et al. ................. 514/385

FOREIGN PATENT DOCUMENTS 190891 8/1986 European Pat. Off. .
200406 12/1986 European Pat. Off. .
206807 12/1986 European Pat. Off. .
266950 5/1988 European Pat. Off. .

Primary Examiner—Mukund J. Shah
Assistant Examiner—Matthew V. Grumbling
Attorney, Agent, or Firm—Richard K. Jackson

[57]  ABSTRACT

A compound of the formula:

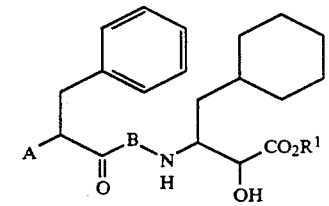

wherein A is

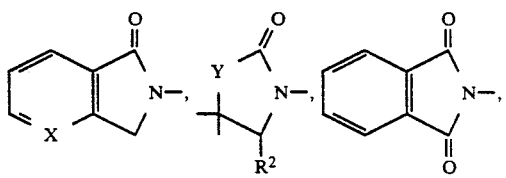

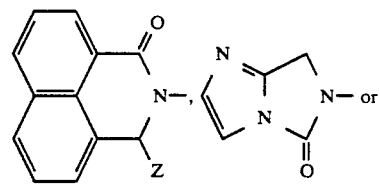

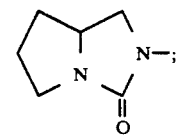

in which X is =CH— or =N—; $R^2$ is hydrogen, alkyl, phenyl, benzyl or phenethyl; Y is —CH$_2$—, —NH— or —O—; and Z is —H$_2$ or =O; B is His, Leu, Ile, Nva, Nle, Ala or Val; and $R^1$ is hydrogen, alkyl, phenyl or phenylalkyl; or a pharmaceutically acceptable salt thereof are renin inhibitors.

2 Claims, No Drawings

PYRROLIMIDAZOLONES USEFUL AS RENIN INHIBITORS

This is a division of application Ser. No. 07/490,810 filed Mar. 8, 1990, now U.S. Pat. No. 5,023,338.

BACKGROUND OF THE INVENTION

The renin-angiotensin system plays a well-defined role in cardiovascular homeostasis. Renin is an aspartic protease which converts angiotensinogen to Angiotensin I, which is acted upon by angiotensin converting enzyme (ACE) to form the vasoactive octapeptide, Angiotensin II. It is now well-known that inhibitors of renin will serve as antihypertensives is mammals. Since HIV protease is in the aspartyl protease class of enzymes (like renin), it is believed that inhibitors of renin will also be effective in the direct or adjunctive treatment of AIDS and other viral diseases.

DESCRIPTION OF THE INVENTION

The compounds of the present invention are renin inhibitors, useful as antihypertensive agents and in the treatment of other disease states amenable to treatment with aspartyl protease inhibitors. The compounds of this invention are described by the following structural formula:

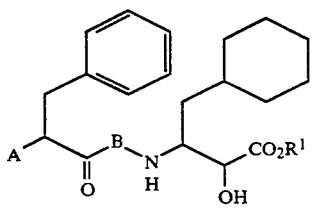

wherein A is

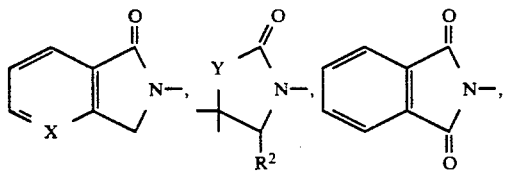

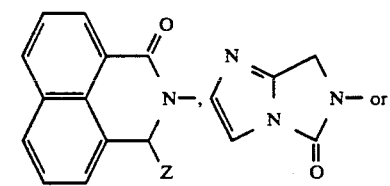

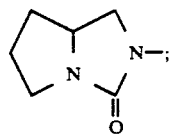

in which

X is =CH— or =N—;
R² is hydrogen, alkyl of 1 to 6 carbon atoms, phenyl, benzyl or phenethyl;
Y is —CH₂—, —NH— or —O—; and
Z is —H₂ or =O;
B is His, Leu, Ile, Nva, Nle, Ala or Val; and
R¹ is hydrogen, alkyl of 1 to 6 carbon atoms, phenyl or phenylalkyl in which the alkyl group has 1 to 6 carbon atoms;

or a pharmaceutically acceptable salt thereof.

Of these compounds, the preferred members are those in which A is

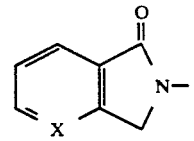

wherein
X is =CH— or =N—;
B is Leu; and
R¹ is isopropyl;

or a pharmaceutically acceptable salt thereof.

In these compounds, the chirality of the amino acids is L unless otherwise specified. The pharmaceutically acceptable salts include e.g. hydrochloride, hydrobromide, sulfate, bisulfate, phosphate, acetate, lactate, mesylate, cirtrate, tartrate and salts produced from similarly known acceptable acids.

The abbreviation ACHBA used infra denotes 3-amino-4-cyclohexyl-2-hydroxy butanoic acid.

The compounds of the invention are prepared by conventional methods. For example, suitably protected amino acids or amino acid derivatives are coupled via a free carboxyl group to an appropriate amino group to form a peptide bond. Acylation or alkylation about the N-terminal amino acid may be carried out as shown:

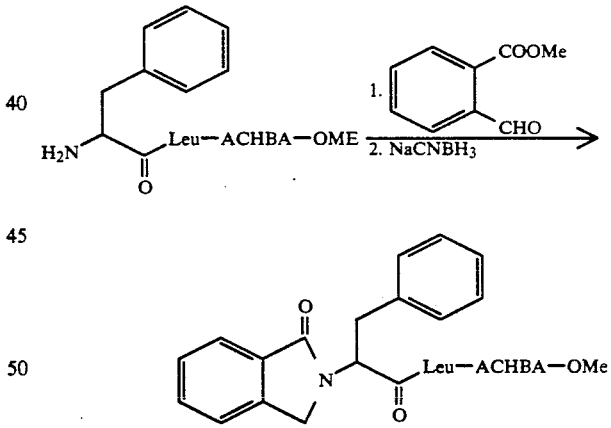

The potent in vitro inhibition of the aspartyl protease renin was established using standard radio immunoassay techniques for the detection of Angiotensin I from an angiotensinogen-like substrate [Haber et al. (1969), J. Clin. Endocrinol. 29, 1349]. The results of these standard test procedures appears at the end of each Example of preparation of the relevant compound, as the percent inhibition of renin activity at $10^{-6}$M concentration of test compound. The compounds of this invention have also shown strong resistance to breakdown by degradative enzymes such as chymotrypsin, following the procedure of Thaisrivongs et al. (1987) J. Med. Chem. 30, 536–541. For example, the compound of Example 1 was nearly unchanged upon incubation with chymotrypsin for one hour (93% remaining compound)

whereas Boc-Phe Leu-ACHBA-OMe was extensively degraded (22% remaining compound) in the same time period. Even after a 24 hour incubation, 68% of the compound of Example 1 remained. In accord with their ability to inhibit the enzyme renin, the compounds of this invention show plasma renin lowering effects and an antihypertensive action in a furosemide-stimulated high-renin model [De Claviere, M. et al. (1985), J. Cardiovascular Pharmacology 7(Suppl. 4), S58-S61] with conscious rhesus monkeys, utilizing intravenous as well as oral dosing. For example, the product of Example 1 administered at 5 mg/kg iv lowered plasma renin activity (PRA) from 45 ng/ml/min to 5 ng/ml/min one half hour post-administration. Mean arterial pressure (MAP) was lowered 25 mm in that time period. Orally at 50 ng/kg, the same compound decreased PRA by 50% with no significant change in MAP one-half hour post-administration.

The following Examples illustrate the production of representative compounds of this invention.

EXAMPLE 1

Beta-[[2-[[2-[1,3-dihydro-1-oxo-2H-isoindol-2-yl]-1-oxo-3-phenylpropyl]amino]-4-methyl-1-oxo-pentyl-]amino]-alphahydroxycyclohexanebutanoic acid methyl ester To a solution of N-tertiary butyloxycarbonyl (BOC) protected, 3-amino-4-cyclohexyl-2-hydroxybutanoic acid methyl ester (1.43 g, 4.54 mmol) in methylene chloride (3.5 mL) at 10° C. was added an equivalent of trifluoroacetic acid (3.5 mL, 45.4 mmol). The cooling bath was removed and after 35 minutes the reaction mixture was concentrated to dryness and residual trifluoroacetic acid was removed as an azeotrope with toluene (2×1 mL) to provide 1.98 g of 3-amino-4-cyclohexyl-2-hydroxybutanoic acid methyl ester, trifluoroacetic acid salt, as an oil.

$^1$H-NMR: (CDCl$_3$, 200 MHz) δ4.35 and 4.63 (2d, 1H, J=2.9 Hz), 3.81 (s, 3H, OCH$_3$), 3.05 to 3.8 (m, 4H), 0.75 to 1.81 (m, 13H, CHn).

FAB-MS (M+H)=216.

To a solution of the product of the preceding paragraph (1.98 g, 6.03 mmol) in methylene chloride (35 mL) at 0° C. was added N-methylmorpholine (0.66 mL, 6.03 mmol), 1-hydroxybenzotriazole hydrate (0.98 g, 7.23 mmol), and BocPheLeu (2.28 g, 6.03 mmol). After stirring 5 minutes, the pH was readjusted to about 6.5-7.0 with additional N-methylmorpholine followed by the addition of 1-cyclohexyl-3-(2-morpholinoethyl) carbodiimide metho-p-toluenesulfonate (2.55 g, 6.03 mmol). After stirring 16 hours, the reaction mixture was quenched with water (50 mL), partitioned, the aqueous layer was diluted with water (100 mL) and extracted with ethyl acetate (2×200 mL). The combined organic layers were washed with water (1×150 mL), 1N HCl (2×100 mL), saturated aqueous NaHCO$_3$ (2×100 mL), saturated aqueous NaCl (1×200 mL), dried over MgSO$_4$, filtered, concentrated, and flash chromatographed (SiO$_2$ gel) with a 10 to 25% gradient EtOAc/CH$_2$Cl$_2$ to provide 1.82 g (69.7% yield) of N-tertiary butyloxycarbonyl-Phe-Leu-3-amino-4-cyclohexyl-2-hydroxybutanoic acid methyl ester as a white solid.

$^1$H-NMR: (CDCl$_3$, 400 MHz) δ7.16 to 7.31 (m, 5H, ArH), 6.29 (m, 1H), 6.22 (m, 1H), 4.86 (m, 1H), 4.25 to 4.39 (m, 2H), 4.14 (bs, 1H) 3.77 and 3.76 (s, 3H, OCH$_3$), 3.41 (bs, 1H), 3.07 (m, 1H), 0.82 to 1.81 (m, 31H, includes 1.39 (s, 9H, C(CH$_3$)$_3$), and 1.18 (dd, 6H, CH(CH$_3$)$_2$).

FAB-MS (M+H)$^+$=576

Elemental analysis for C$_{31}$H$_{49}$N$_3$O$_7$; Calc'd: C, 64.67; H, 8.58; N, 7.30, Found: C, 64.47; H, 8.47; N, 7.19.

To a solution of the product of the preceding paragraph (0.070 g, 0.122 mmol) in CH$_2$Cl$_2$ (1 mL) at 0° C. was added excess CF$_3$COOH. After stirring 30 minutes the reaction was concentrated to dryness and the residual CF$_3$CO$_2$H was removed as an azeotrope with toluene (2×1 mL) to provide 0.097 g of the deprotected amine salt.

$^1$H-NMR: (CDCl$_3$, 200 MHz) δ7.68 (d, 1H), 7.19 to 7.38 (m, 5H, ArH), 7.08 (d, 1H), 4.23 to 4.39 (m, 3H), 3.68 (s, 3H), 3.23 (d, 2H), 0.79 to 1.68 (m, 22H).

To a solution of crude amine salt prepared in the preceding paragraph (1.52 g, 2.58 mmol) in methanol (20 mL) at room temperature was added N-methylmorpholine (0.28 mL, 2.58 mmol, additional N-methylmorpholine was added to pH=7, about 0.1 mL) and 2-methoxycarbonylbenzaldehyde (0.68 g, 4.12 mmol), and after 5 minutes NaCNBH$_3$ (0.21 g, 3.35 mmol). A slight effervescence was noted. After heating at 45° C. for 16 hours the reaction mixture was cooled, quenched with water (50 mL), and extracted into ethyl acetate (3×100 mL). The combined organic extracts were washed with saturated aqueous NaHCO$_3$ (2×50 mL), 1N HCl (2×50 mL), dried over MgSO$_4$, filtered, concentrated, and flash chromatographed (SiO$_2$ gel, 1% MeOH/CHCl$_3$) to provide 0.657 g (58% yield) of the title compound as a white solid.

Elemental analysis for C$_{34}$H$_{45}$N$_3$O$_6$; Calc'd: C, 69.01; H, 7.66; N, 7.10; Found: C, 68.88; H, 7.51; N, 6.69.

% I=97%

EXAMPLE 2

Beta-[[2-[[2-[1,3-dihydro-1-oxo-2H-isoindol-2-yl]-1-oxo-3-phenylpropyl]amino]-4-methyl-1-oxo-pentyl-]amino]-alphahydroxycyclohexanebutanoic acid 1-methylethyl ester To a slurry of Phe (23.06 g, 139.6 mmol) in MeOH (400 mL) was added 2-methoxycarbonylbenzaldehyde (27.5 g, 167.5 mmol) and after 5 minutes, NaCNBH$_3$ (10.53 g, 167.5 mmol). After refluxing overnight, the reaction mixture was partially concentrated. The reduced volume reaction mixture was quenched with saturated NaHCO$_3$ (about 1 L) and washed with diethyl ether (2×500 mL). The aqueous layer was adjusted to pH 2.5 with solid NaHSO$_4$ and extracted into EtOAc (4×400 mL). The combined organic extracts were washed with saturated NaCl (500 mL), dried over MgSO$_4$, filtered, concentrated, precipitated out of EtOAc with diethyl ether, washed with diethyl ether and dried in vacuo to provide 20.57 g (55.1% yield) of N-(1-oxo-2H-isoindol-2-yl-1-phenylalanine) as a white solid.

$^1$H-NMR: (CDCl$_3$; 200 MHz) δ7.84 (d, 1H), 7.16 to 7.58 (m, 8H), 5.17 (q, 1H), 4.29 (q, 2H), 3.52 (m, 2H).

FAB-MS (M+H)$^+$=282.

In flame dried glassware with a nitrogen atmosphere, to the acid prepared in the preceding paragraph (0.33 g, 1.24 mmol) in anhydrous ethylacetate (10 mL) was added at 0° C. N-methylmorpholine (0.14 mL, 1.24 mmol). After further cooling to −10° C. isobutyl-chloroformate (0.16 mL, 1.24 mmol) was added. After 5 minutes Leu methyl ester HCl (0.23 g, 1.24 mmol) was added and then the white slurry was basified with N- methylmorpholine (0.14 mL, 1.24 mmol, pH about 7.5). The reaction mixture was warmed to room temperature and after 45 minutes quenched with saturated NaHCO$_3$ (about 30 mL) and extracted into EtOAc (3×50 mL). The combined organic extracts were washed with saturated NaHCO$_3$ (1×50 mL), 1N HCl (2×50 mL), saturated NaCl (1×50 mL), dried over MgSO$_4$, filtered, concentrated, and flash chromatographed (SiO$_2$ gel, 10–20% EtOAc/CH$_2$Cl$_2$ gradient) to provide 0.44 g (86.6% yield) of the N-(1-oxo-2H-isoindol-2-yl)-Phe-Leu-methyl ester as a white foam.

$^1$H-NMR: (CDCl$_3$; 200 MHz) δ7.83 (d, 1H), 7.39 to 7.54 (m, 3H), 7.23 (m, 5H), 6.68 (d, 1H), 5.15 (dd, 1H), 4.50 (m, 1H), 4.43 (s, 2H), 3.67 (s, 3H, OCH$_3$), 3.34 (dq, 2H), 1.5 (m, 3H), 0.75 (d, 6H, 2CH$_3$).

FAB-MS (M+H)$^+$=409.

To a solution of the compound produced in the preceding paragraph (0.43 g, 1.06 mmol) in MeOH (3.3 mL) was added 1N NaOH (1.1 mL, 1.06 mmol). On 30 minute intervals, additional 1N NaOH (0.5 mL, 0.5 mmol) was added as needed by thin layer chromatographic analysis (20% EtOAc/CH$_2$Cl$_2$). After 1.5 hours, the reaction mixture was diluted with H$_2$O (50 mL) and washed with diethyl ether (2×50 mL). The aqueous layer was acidified to pH about 2.0 with solid NaHSO$_4$ and extracted with EtOAc (3×50 mL). The combined organic extracts were washed with saturated NaCl, dried over MgSO$_4$, filtered, and concentrated to provide 0.39 g (93.4% yield) of N-(1-oxo-2H-isoindol-2-yl)-Phe-Leu as a white solid.

$^1$H-NMR: (CDCl$_3$; 200 MHz) δ7.80 (d, 1H), 7.41 to 7.58 (m, 3H), 7.14 to 7.23 (m, 5H), 5.32 (q, 1H), 4.56 (m, 1H), 4.50 (s, 2H), 3.31 (dq, 2H, J=14.5 hz), 1.56 (m, 3H), 0.78 (d, 6H, 2CH$_3$).

FAB-MS (M+H)$^+$=395.

Elemental analysis for C$_{23}$H$_{26}$N$_2$O$_4$.¼H$_2$O; Calc'd: C, 69.24; H, 6.64; N, 7.02; Found: C, 69.51; H, 6.78; N, 6.76.

The C-terminal portion of the title compound was prepared as follows:

To a solution of N-tertiary butyloxycarbonyl-3-amino-4-cyclohexyl-2-hydroxybutanoic acid (1.11 g, 3.70 mmol) in anhydrous diethyl ether (15 mL) was added isopropyl alcohol (12.8 mL, 0.148 mol), triphenylphosphine (1.10 g, 4.81 mmol), and diethylazidodicarboxylate (0.80 mL, 4.81 mmol). After stirring 15 minutes, the yellow solution was quenched with saturated NaHCO$_3$ (150 mL) and extracted into diethyl ether (3×100 mL). The combined extracts were washed with saturated NaHCO$_3$ (1×100 mL), 1N HCl (2×100 mL), saturated NaCl (1×200 mL), dried over MgSO$_4$, filtered, concentrated, and flash chromatographed (SiO$_2$ gel; 4% to 8% diethyl ether/CH$_2$Cl$_2$ gradient) to provide 1.13 g (89.3% yield) of the isopropyl ester as a light yellow oil.

$^1$H-NMR: (CDCl$_3$; 200 MHz) δ5.08 (m, 1H), 4.59 and 4.7 (2d, 1H), 4.2 (m, 2H), 3.04 and 3.11 (2d, 1H), 0.8 to 1.9 (28H, including 1.39 and 1.45 (2s, 9H, C(CH$_3$)$_3$) and 1.26 and 1.30 (2s, 6H, $^i$Pr).

FAB-MS (M+H)$^+$=344.

To a solution of the compound produced in the preceding paragraph in CH$_2$Cl$_2$ (1 mL) at 10° C. was added trifluoroacetic acid (1 mL). After 30 minutes, the reaction mixture was concentrated to dryness and azeotroped with toluene (2×1 mL) to provide 0.11 g of the trifluoroacetate salt as a foam.

$^1$H-NMR: (CDCl$_3$; 200 MHz) δ7.7 (bs, 2H), 5.1 (m, 1H), 4.2 to 5.05 (2H), 3.81 (1H), 0.8 to 1.8 (19H).

FAB-MS (M+H)$^+$=244 (free base).

Then the previously prepared isoindol-Phe-Leu intermediate was reacted with the amine salt as follows:

To a solution of trifluoroacetate salt prepared in the preceding paragraph (0.11 g, 0.29 mmol) in CH$_2$Cl$_2$ (5 mL) at 10° C. was added N-methyl morpholine (0.034 mL, 0.31 mmol) to pH about 6.5, 1-hydroxybenzotriazole hydrate (0.05 g, 0.37 mmol), N-(1-oxo-2H-isoindol-2-yl)-Phe-Leu (0.123 g, 31 mmol), and after adjusting the pH to about 6.5 with additional N-methylmorpholine, 1-cyclohexyl-3-(2-morpholino ethyl) carbodiimide metho-p-toluene sulfonate (0.132 g, 0.31 mmol) was added. The reaction mixture was allowed to warm and stirred overnight and then quenched with water (50 mL) and extracted into EtOAc (3×50 mL). The combined extracts were washed with H$_2$O (50 mL), 1N HCl (2×50 mL), saturated NaHCO$_3$, (2×50 mL) saturated NaCl, dried over MgSO$_4$, filtered, concentrated, flash chromatographed (SiO$_2$ gel) first in 25% to 35% EtOAc/CH$_2$Cl$_2$ then 45% EtOAc/Hexane to provide the title compound as two diastereomers (A) 0.067 g and (B) 0.012 g (combined 43.6% yield) as foams. A=100% pure; B=1:7 (mixture of A and the other diastereomer).

Diastereomer A $^1$H-NMR: (CDCl$_3$, 400 MHz) δ7.83 (d, 1H, J=7.5 Hz, 7.53 (t, 1H), 7.45 (t, 1H), 7.39 (d, 1H), 7.17 to 7.25 (m, 5H), 6.80 (d, 1H), 6.12 (d, 1H), 5.05 (dd, 1H), 5.0 (dd, 1H), 4.30 to 4.45 (m, 3H, includes 4.37 (dd, 2H, J=42 Hz and 17 Hz), 4.21 (m, 1H), 4.05 (dd, 1H, J=4.8 Hz and 1.9 Hz), 3.38 (dq, 2H), 3.19 (d, 1H, J=4.8 Hz), 1.82 (d, 1H), 1.28 to 1.69 (m, 10H), 1.26 (d, 3H, OCHCH$_3$, J=2.3 Hz), 1.24 (d, 3H, OCHCH3, J=2.3 Hz), 0.83 to 1.21 (m, 5H), 0.76 (d, 3H, CH$_3$, J=6.5 Hz), 0.71 (d, 3H, CH$_3$, J=6.5 Hz).

FAB-MS (M+H)$^+$=620.

Elemental analysis for C$_{36}$H$_{49}$N$_3$O$_6$.½H$_2$O; Calc'd: C, 68.76; H, 8.01; N, 6.68; Found: C, 68.95; H, 8.14; N, 6.60. % I=98%

Diastereomer B (12.5% Diastereomer A)

$^1$H-NMR: (CDCl$_3$, 400 MHz) δ7.83 (d, 1H, J=7.5 Hz), 7.53 (t, 1H), 7.46 (t, 1H), 7.39 (d, 1H, J=7.5 Hz), 7.16 to 7.25 (m, 5H), 6.98 (d, 1H), 6.22 (d, 1H), 5.07 (m, 2H), 4.24 to 4.44(m, 3H, includes 4.36 (dd, 2H), J=51 Hz and 17 Hz), 4.16 (d, 1H), 3.38 (dq, 2H), 1.82 (d, 1H), 0.70 to 1.70 (m, 21H, includes 1.27 (d, 3H, OCHCH$_3$, J=4.3 Hz), 1.25 (d, 3H, OCHCH$_3$, J=4.2 Hz), 0.80 (d, 3H, CH$_3$, J=6.5 Hz), and 0.73 (d, 3H, CH$_3$, J=6.5 Hz).

FAB-MS (M+H)$^+$=620.

EXAMPLE 3

Beta-[[2-[[-2-(1,3-dihydro-1-oxo-2H-pyrrolo[3,4-b]pyridin-2-yl)-1-oxo-3-phenylpropyl]amino]-4-methyl-1-oxopentyl]amino]-alphahydroxycyclohexanebutanoic acid methyl ester To a solution of the trifluoroacetate salt of Phe-Leu-OMe (0.188 g, 0.392 mmol) in MeOH (3 mL) was added at 10° C. N-methylmorpholine (0.08 mL, 0.73 mmol to pH=7), 2-formyl-3-pyridinecarboxylic acid ethyl ester (0.070 g, 0.392 mmol), and NaCNBH$_3$ (0.032 g, 5.09 mmol) (effervescence). After heating to reflux for 3 hours the reaction mixture was stirred overnight before quenching with saturated NaHCO$_3$ (25 mL) and extracting into EtOAc (3×25 mL). The combined organic extracts were washed with brine, dried over MgSO$_4$, concentrated to dryness, flash chromatographed (SiO₂ gel; 20% EtOAc/CH₂Cl₂), redissolved in toluene, refluxed 17 hours, and reconcentrated to provide 0.062 g (38%) of N-(7-aza-1-oxo-2H-isoindol-2-yl)-Phe-Leu-O methyl as a foam.

¹H-NMR: (CDCl₃, 200 MHz) δ8.71 (d, 1H), 8.07 (d, 1H), 7.37 (dd, 1H), 7.14 to 7.28 (m, 5H), 6.75 (d, 1H, NH), 5.26 (dd, 1H), 4.56 (m, 3H, includes 4.56 (q, 2H), 3.68 (s, 3H, OCH₃), 3.18 to 3.50 (dq, 2H, OCH₂), 1.51 (m, 3H), 0.79 (d, 6H, CH₃).

To a solution of the compound produced in the preceding paragraph (0.062 g, 0.151 mmol) in MeOH (0.5 mL) at 10° C. was added 1N NaOH (0.15 mL, 0.151 mmol). On 30 minute intervals, additional 1N NaOH (0.075 mL, 0.075 mmol) was added as needed by thin layer chromatographic analysis (20% EtOAc/CH₂Cl₂). After 1 hour, the reaction mixture was diluted with H₂O (25 mL) and washed with diethyl ether (2×25 mL). The aqueous layer was acidified with solid NaHSO₄ (pH=4) and extracted into EtOAc (3×25 mL). The organic extracts were washed with saturated NaCl, dried over MgSO₄, filtered, and concentrated to provide 0.056 g (91% yield) of N-(7-aza-1-oxo-2H-isoindol-2-yl)-Phe-Leu-OH as a white solid.

¹H-NMR: (CDCl₃, 200 MHz) δ8.70 (d, 1H), 8.61 (bs, 1H), 8.08 (d, 1H), 7.38 (dd, 1H), 7.10 to 7.28 (m, 5H), 5.37 (dd, 1H), 4.63 (m, 3H, includes 4.63 (q, 2H)), 3.35 (dq, 2H), OCH₂), 1.60 (m, 3H), 0.82 (d, 6H, CH₃).

FAB-MS (M+H)⁺ = 396

To a solution of 3-amino-4-cyclohexyl-2-hydroxybutanoic acid methyl ester trifluoroacetate salt (0.054 g, 0.136 mmol) in CH₂Cl₂(4 mL) at 0° C. was added N-methylmorpholine (0.015 mL, 0.136 mmol), 1-hydroxybenzotriazole hydrate (0.022 g, 0.164 mmol), the acid prepared in the preceding paragraph (0.054 g, 0.136 mmol), and (after readjusting the pH=6.5 to 7.0 with N-methylmorpholine) 1-cyclohexyl-3-(2-morpholinoethyl)carbodiimide metho-p-toluenesulfonate (0.058 g, 0.136 mmol). After stirring overnight the reaction mixture was quenched with H₂O (20 mL) and extracted into EtOAc (3×25 mL). The combined organic extracts were washed with H₂O (20 mL), 0.5N HCl (2×25 mL), saturated NaHCO₃ (2×25 mL), saturated NaCl, dried over MgSO₄, filtered, concentrated, and flash chromatographed (SiO₂ gel; 1/10/89 MeOH/EtOAc/CH₂Cl₂) to provide 0.045 g (55% yield) of the title compound as a foam.

¹H-NMR: (CDCl₃, 400 MHz) δ8.70 (dd, 1H, J=4.9 Hz and 1.3 Hz), 8.08 (dd, 1H, J=7.7 Hz and 1.5 Hz), 7.37 (m, 1H), 7.15 to 7.25 (m, 5H), 6.61 and 6.82 (2d, 1H), 6.07 and 6.18 (2d, 1H), 5.11 (m, 1H), 4.45 (q, 2H), 4.42 (m, 1H), 4.22 (m, 1H), 4.12 (dd, 1H), 3.72 and 3.75 (2s, 3H, OCH₃), 3.22 to 3.55, m, 3H), 0.73 to 1.80 (m, 22H).

FAB-MS (M+H)⁺ = 593.

Elemental analysis for C₃₃H₄₄N₄O₆·H₂O; Calc'd: C, 64.90; H, 7.57; N, 9.17; Found: C, 64.71; H, 7.22; N, 9.02.
% I=89%

EXAMPLE 4

Beta-[[2-[[2-(1,3-dihydro-1-oxo-2H-isoindol-2-yl)-1-oxo-3-phenylpropyl]amino]-3-(1H-imidazol-4-yl)-1-oxopropyl]amino]-alphahydroxycyclohexane butanoic acid methyl ester To a chilled (ice-bath) solution of 3-amino-4-cyclohexyl-2-hydroxybutanoic acid methyl ester trifluoroacetate salt (0.46 mmol) in 2 mL CH₂Cl₂ was added 51 mL of N-methylmorpholine, 282 mg (0.69 mmol) of Boc-(Ts)-His, and 132 mg (0.69 mmol) of 1-(3-Dimethyl aminopropyl)-3-ethyl-carbodiimide hydrochloride. Excess N-methylmorpholine was added to bring the pH of the mixture to 6–7. The solution was allowed to gradually warm to room temperature overnight. Excess EtOAc was added and the organic layer was washed with H₂O, saturated sodium bicarbonate, and brine. The ethyl acetate layer was dried, filtered, and concentrated in vacuo. Column chromatography (SiO₂ gel; 2–5% MeOH/CHCl₃) yielded 0.19 g (69% yield) of αN-(t-butyloxycarbonyl)-$^{im}$N-tosyl-His-3-amino-4-cycloalkyl-2-hydroxy-butanoic acid methyl ester.

¹H-NMR (CDCl₃, 200 MHz) δ7.05–8.00 (m, 6H, aromatic), 6.53 and 6.28 (2d, J=9 Hz), 5.67–5.85 (m, 1H), 4.03–4.45 (m, 3H), 3.76 and 3.73 (2S, minor and major OCH₃), 2.80–3.07 (m, 2H), 2.45 (s, 3H, tosyl CH₃), 0.70–1.80 (m, 22H, including 2s, 1.44 and 1.43, major and minor Boc)

The product of the preceding paragraph (0.179 g, 0.3 mmol) was subjected to the deprotection procedure presented in paragraph 1 of Example 1 to give the TFA salt (no Boc group by 200 MHz NMR), which was coupled directly to N-(1-oxo-2H-isoindol-2-yl)-L-phenylalanine (0.11 g, 0.39 mmol) utilizing the procedure of the preceding paragraph. Some detosylation occurred in the coupling reaction. Column chromatography (SiO₂ gel; 8% MeOH/CHCl₃) of the crude material gave 0.040 g (21% yield) of the detosylated final product (an additional 0.2 mmol (67% yield) of tosylated product was also recovered).

¹H-NMR (CDCl₃, 400 MHz) δ6.68–7.92 (m, 11H, aromatic), 6.34 (d, 1H, J=8.7 Hz) 5.04–5.16, (m, 1H), 4.24–4.72 (m, 5H), 3.76 and 3.71 (2s, 3H, OCH₃), 3.48–3.68 (m, 2H), 2.82–3.36 (m, 3H), 0.75–1.80 (m, 13H)

FAB-MS (M+H)⁺ = 616

Elemental analysis for C₃₄H₄₁N₅O₆·1¾H₂O; Calc'd: C, 63.09; H, 6.93; N, 10.82; Found: C, 62.91; H, 6.26; N, 10.68.
% I=84%

EXAMPLE 5

Beta-[[2-[[2-(1,3-dihydro-1-oxo-2H-isoindol-2-yl)-1-oxo-3-phenylpropyl]amino]-3-(1H-imidazol-4-yl)-1-oxopropyl]amino]-alphahydroxycyclohexanebutanoic acid 1-methylethyl ester The trifluoroacetate salt of 3-amino-4-cyclohexyl-2-hydroxybutanoic acid isopropyl ester (2.73 mmol) was coupled with Boc-(Ts)-L-His (1.7 g, 4.15 mmol) utilizing the procedure of preceding Example 4. Column chromatography (SiO₂ gel; 2% MeOH/CHCl₃) of the crude material yielded 1.31 g (76% yield) of pure αN-(t-butyloxycarbonyl)-$^{im}$N-tosyl-His-3-amino-4-cyclohexyl-2-hydroxybutanoic acid isopropyl ester with a diastereomeric ratio of about 5:1.

¹H-NMR (CDCl₃, 200 MHz) δ7.1–8.0 (m, 6H, aromatic), 6.59 and 6.30 (2d, J=10 Hz), 5.50–5.89 (m, 1H), 4.90–5.15 (m, 1H), 3.97–4.70 (m, 4H), 2.75–3.13 (m, 3H), 2.44 (s, 3H, tosyl CH₃), 0.70–1.90 (m, 28H, including 2s, 1.43 and 1.40, major and minor Boc)

FAB-MS (M+H)⁺ = 635.

The product of the preceding paragraph (0.327 g, 0.52 mmol) was subjected to the deprotection procedure presented in paragraph 1 of Example 1 to give the TFA salt (>100%), which was coupled directly to N-(1-oxo-2H-isoindol-2-yl)-L-phenylalanine (0.219 g, 0.78 mmol) utilizing the procedure of Example 4. Some detosylation occurred during the coupling reaction. Column chromatography (SiO2 gel; 2-5%) MeOH/CHCl3) of the crude material gave several products including 0.121 g (29% yield) of tosylated product, and 0.082 g (24%) of the detosylated title compound as a white solid.

FAB-MS (M+H)+ = 644.

% I = 83%

EXAMPLE 6

Beta-[[2-[[2-(1,3-dihydro-1,3-dioxo-2H-isoindol-2-yl)-1-oxo-3-phenylpropyl]amino]-4-methyl-1-oxopentyl]amino]-alphahydroxycyclohexanebutanoic acid methyl ester The title compound was prepared from N-phthalyl-Phe (0.028 g, 95 μmol) and TFA-Leu-3-amino-4-cyclohexyl-2-hydroxy-butanoic acid methyl ester (81.7 μmol) following the procedure of Example 1, second paragraph. Column chromatography (SiO2 gel; 2% MeOH/CHCl3) yielded 0.036 g (73% yield) of pure compound with a diastereomeric ratio of 28:1.

$^1$H-NMR (CDCl3, 400 MHz) d 7.69-7.82 (m, 4H, aromatic), 7.11-7.23, (m, 5H, aromatic), 6.51 and 6.44 (2d, 1H, J=7.7 Hz), 6.27 and 6.15 (2d, 1H, J=9.3 Hz), 5.13 (dd, 2H, J=9.3 Hz, 7.2 Hz), 4.12-4.43 (m, 3H), 3.72 (s, 3H, OCH3), 3.26-3.54 (m, 2H), 0.90-1.82 (m, 22H)

FAB-MS (M+H)+ = 606.

Elemental analysis for $C_{34}H_{43}N_3O_7 \cdot 1.5H_2O$; Calc'd: C, 64.54; H, 7.33; N, 6.64; Found: C, 64.49; H, 7.03; N, 6.48.

% I = 45%

EXAMPLE 7

Beta-[[2-[[2-(1,3-dihydro-1,3-dioxo-2H-isoindol-2-yl)-1-oxo-3-phenylpropyl]amino]-3-(1H-imidazol-4-yl)-1-oxopropyl]amino]-alphahydroxycyclohexanebutanoic acid methyl ester 3-Amino-4-cyclohexyl-2-hydroxybutanoic acid methyl ester trifluoroacetate (0.66 mmol) was coupled with Boc (Ts)-His (0.295 g, 0.72 mmol) following the procedure disclosed in the second paragraph of Example 1, supra. Since the 1-hydroxybenzotriazole used in the reaction caused some detosylation, column chromatography (SiO2 gel; 2-5% MeOH/CHCl3) yielded a small amount of detosylated intermediate (0.036 g, 12%), which was utilized in the next step.

$^1$H-NMR (CDCl3, 200 MHz) δ7.59 (brs, 1H), 6.88 (brs, 1H), 5.77 and 5.52 (2d, J=7 Hz), 5.07 (d, J=10 Hz), 4.10-4.65 (m, 3H), 3.75 and 3.74 (2s, 3H, OCH3), 2.90-3.25 (m, 2H), 0.70-1.85 (m, 22H, includes 1.45, s, Boc)

The Boc protected compound was subjected to deprotection following the procedure presented in paragraph 1 of Example 1, supra to give the TFA salt (no Boc by NMR), which was coupled directly to phthalyl-Phe (0.023 g, 0.074 mmol) utilizing the procedure of paragraph 2 of Example 1 to yield 0.018 g (40% yield) of the title compound as a light yellow solid.

$^1$H-NMR (CDCl3, 400 MHz) δ7.04-7.92 (m, 10H, aromatic), 6.86 (bs, 1H), 4.96-5.20 (m, 1H), 4.10-4.70 (m, 3H), 2.92-3.82 (m, 7H, including 3.75 and 3.74, 2s, OCH3), 0.80-1.84 (m, 13H)

FAB-MS (M+H)+ = 630.

% I = 9%

EXAMPLE 8

Beta-[[2-[[2-(1,3-dioxo-1H-benz[de]isoquinolin-2(3H)-yl)-1-oxo-3-phenylpropyl]amino]-4-methyl-1-oxopentyl]amino]-alphahydroxycyclohexanebutanoic acid methyl ester To a solution of N-(t-butyloxycarbonyl)-Phe-Leu-3-amino-4-cyclohexyl-2-hydroxybutanoic acid methyl ester (0.318 g, 0.553 mmol) in CH2Cl2 (3 mL) at 15° C. was added CF3COOH (3 mL). After stirring 30 minutes, the reaction mixture was diluted with CH2Cl2 (20 mL) and basified with saturated NaHCO3 (50 mL). The aqueous layer was extracted in CH2Cl2 (2×40 mL). The combined organic layers were washed with brine, dried over MgSO4, filtered, and concentrated to provide 0.219 g (83.4% yield) of the free amine as a white foam.

$^1$H-NMR: (CDCl3, 400 MHz) δ7.66 and 7.72 (2d, 1H), 7.20 to 7.34 (m, 5H), 6.51 and 6.43 (2d, 1H), 4.34 (m, 2H), 4.15 (d, 1H), 3.77 and 3.79 (2s, 3H, OCH3), 3.63 (dd, 1H), 3.23 (dd, 1H), 2.73 (dd, 1H), 0.91 to 1.76 (m, 22H, includes 0.91 (dd, 6H, CH(CH3)2)

FAB-MS (M+H)+ = 476.

To a solution of the amine produced in the preceding paragraph (0.08 g, 0.17 mmol) in toluene (5 mL) was added 1,8-napthalic anhydride (0.03 g, 0.17 mmol). After 2 hours at reflux MgSO4 was added (tip of spatula). After refluxing overnight the reaction was cooled to room temperature, quenched with 1N HCl (25 mL), and extracted into CH2Cl2 (3×30 mL). The combined extracts were washed in 1N HCl (1×30 mL), saturated NaHCO3 (2×30 mL), saturated NaCl (1×30 mL), dried over MgSO4, filtered, concentrated, and flash chromatographed (SiO2 gel; 20-30% EtOAc/CH2Cl2 gradient) to provide 0.03 g (28% yield) of the title compound as a hard foam.

$^1$H-NMR: (CDCl3; 400 MHz) δ8.60 (d, 2H), 8.24 (d, 1H), 7.77 (t, 2H), 7.20 to 7.35 (m, 5H), 6.73 (d, 1H), 6.09 (dd, 1H), 5.94 (d, 1H), 4.45 (m, 1H), 4.29 (m, 1H), 4.19 (dd, 1H), 3.88 (d, 1H), 3.40 to 3.95 (m, 5H, includes 3.66 (s, 3H, OCH3)), 0.80 to 1.88 (m, 16H), 0.76 (t, 6H, CH(CH3)2).

FAB-MS (M+H)+ = 656.

Elemental analysis for $C_{38}H_{45}N_3O_7 \cdot 1.5H_2O$; Calc'd: C, 66.84; H, 7.08; N, 6.15; Found: C, 67.09; H, 6.87; N, 6.22.

% I = 74%

EXAMPLE 9

Beta-[[2-[[2-[4,5,5-trimethyl-2-oxo-3-oxazolidinyl]-1-oxo-3-phenylpropyl]amino]-4-methyl-1-oxo-pentyl]amino]-alphahydroxycyclohexanebutanoic acid methyl ester To a solution of TFA-Phe-Leu-OMe (0.56 mmol) in MeOH was added N-methylmorpholine (0.93 mL, pH=7), 3-hydroxy-3-methyl-2-butanone (0.84 mmol), and NaCNBH3 (0.72 mmol) under a N2 atmosphere. The reaction mixture was stirred overnight at room temperature and quenched with 50 mL of saturated NaHCO3. The aqueous layer was extracted 3 times with EtOAc (25 mL). The combined organic layers were washed with brine, dried over MgSO4, filtered, concentrated, and then flash chromatographed (1-3% MeOH/CH2Cl2; SiO2 gel) to yield 0.17 g (80% yield) of N-(2-hydroxy-2-methyl-1-methylpropyl)-L-phenylalanyl-L-leucine methyl ester as an oil.

$^1$H-NMR (CDCl3, 200 MHz) δ8.32 (d, 1H), 7.53 (d, 1H), 7.22-7.35 (m, 5H), 4.64 (m, 1H), 3.71 and 3.72 (2s, 3H), 2.98-3.47 (m, 3H), 2.25-2.77 (m, 2H), 0.65-1.67 (m, 18H)

FAB-MS (M+H)+ =379.

To a solution of the product of the preceding paragraph (0.34 mmol) in CH$_2$Cl$_2$ (8 mL) at 0° C. was added pyridine (0.042 mL) and phosgene (0.23 mL, 1.93 in toluene). After 30 minutes, an additional portion of pyridine (0.02 mL) and phosgene (0.1 mL) were added. The reaction was stirred an additional 30 minutes at 0° C. and then quenched with saturated NaHCO$_3$ (50 mL). The aqueous layer was extracted with EtOAc (3×50 mL), the organic layers were combined and washed with 1N HCl, brine, dried over MgSO$_4$, filtered, concentrated, and flash chromatographed (3-5% EtOAc/CH$_2$Cl$_2$; SiO$_2$ gel) to provide 0.107 g (79.4% yield) of N-(4,5,5-trimethyl-2-oxo-3-oxazolidinyl)-L-phenylalanyl-L-leucine methyl ester as a light yellow oil.

$^1$H-NMR (CDCl$_3$, 200 MHz) δ7.58 (m, 1H), 7.20 (m, 5H), 4.47 (m, 1H), 4.28 (m, 1H), 3.65 and 3.66 (2s, 3H), 3.30-3.81 (m, 3H), 0.75-1.71 (m, 18H)

FAB-MS (M+H)+ =405.

To a solution of the product of the preceding paragraph (0.26 mmol) in MeOH (1 mL) was added 0.263 mL of 1N NaOH and the reaction mixture was stirred at room temperature for 30 minutes, at which time an additional 0.1 mL of 1N NaOH was added. The reaction mixture was stirred 30 minutes and then quenched with H$_2$O. The aqueous layer was washed (2×25 mL) with diethyl ether and the pH was lowered to about 3 with solid NaHSO$_4$, and was then extracted (3×25 mL) with EtOAc. The organic layers were washed with brine, dried over MgSO$_4$, filtered, and concentrated to yield 0.0965 g (96.8% yield) of N-(4,5,5-trimethyl-2-oxo-3-oxazolidinyl)-Phe-Leu-OH [FAB-MS (M+H)+ =391] which was directly coupled to the TFA salt from the first paragraph of Example 1 (0.28 mmol) utilizing the procedure of the second paragraph of Example 2. The crude product was flash chromatographed (10-20% EtOAc/CH$_2$Cl$_2$; SiO$_2$ gel) to provide 0.0699 (42% yield) of the title compound as an off-white solid. HPLC indicated a diastereomeric ratio of 2 to 1.

$^1$H-NMR (CDCl$_3$, 400 MHz) δ7.26-7.38 (m, 5H), 6.99 and 7.45 (2d, 1H), 6.19 and 6.27 (2d, 1H), 4.47 (m, 1H), 4.32 (m, 1H), 4.17 (m, 1H), 3.94 (m, 1H), 3.84 (s, 3H), 3.22-3.68 (m, 4H), 0.83-1.92 (m, 31H)

FAB-MS (M+H)+ =588.

Elemental analysis for C$_{32}$H$_{49}$N$_3$O$_7$.¼H$_2$O; Calc'd: C, 64.40; H, 8.44; N, 7.04; Found: C, 64.20; H, 8.34; N, 6.93. % I=76%

EXAMPLE 10

Beta-[[2-[[2-[5,5-dimethyl-2-oxo-3-oxazolidinyl]-1-oxo-3-phenylpropyl]amino]-4-methyl-1-oxo-pentyl]amino]-alphahydroxycyclohexanebutanoic acid methyl ester To a solution of Phe-Leu-OMe (0.69 mmol) in CH$_2$Cl$_2$ (1 mL) was added dimethyl propylene oxide (0.075 mL). The reaction mixture was stirred at room temperature overnight, however, no change was observed. Two additional mLs of the oxide were added and then the reaction mixture was transferred with EtOH (excess) to a closed tube reactor, heated to 100° C. for 5 hours, stirred at room temperature for 2 days, and concentrated to yield 0.24 g of N-(2-hydroxy-2-methylpropyl)-L-phenylalanyl-L-leucine methyl ester.

$^1$H-NMR (CDCl$_3$, 200 MHz) δ7.76 (d, 1H), 4.62 (m, 1H), 3.69 (s, 3H), 3.13-3.35 (m, 2H), 2.36-2.74 (m, 3H), 1.57 (m, 2H), 0.80-1.30 (m, 15H).

FAB-MS (M+H)+ =365.

The product of the preceding paragraph (0.63 mmol) was cyclized utilizing the procedure of Example 9 to yield, after flash chromatography (5% Et$_2$O/CH$_2$Cl$_2$; SiO$_2$ gel), 0.089 g (36% of theory) of N-(5,5-dimethyl-2-oxo-3-oxazolidinyl)-L-phenylalanyl-L-leucine methyl ester.

$^1$H-NMR (CDCl$_3$, 200 MHz) δ7.25 (m, 5H), 6.48 (d, 1H), 4.60 (m, 2H), 3.70 (s, 3H), 3.15 (m, 4H), 1.61 (m, 3H), 1.34 (s, 3H), 1.17 (s, 3H), 0.92 (d, 6H).

FAB-MS (M+H)+ =391.

The ester of the preceding paragraph (0.23 mmol) was deprotected utilizing the procedure of Example 2, third paragraph, to yield 0.043 g of the acid, which was directly coupled to the TFa salt from the first paragraph of Example 1 (0.12 mmol) utilizing the procedure of the second paragraph of Example 2 to yield, after flash chromatography (5-10% Et$_2$O/CH$_2$Cl$_2$; SiO$_2$ gel), 0.029 g (56% yield) of the title compound. HPLC showed a diastereomeric ratio of approximately 9 to 1.

$^1$H-NMR (CDCl$_3$, 400 MHz) δ7.23-7.33 (m, 5H), 6.55 and 6.70 (2d, 1H), 6.02 and 6.18 (2d, 1H), 4.59 (m, 1H), 4.41 (m, 1H), 4.27 (m, 1H), 4.14 (dd, 1H), 3.77 and 3.79 (2s, 3H), 3.04-3.28 (m, 4H), 1.11-1.84 (m, 16H), 0.79-0.97 (m, 6H).

FAB-MS (M+H)+ =574.

Elemental analysis for C$_{31}$H$_{47}$N$_3$O$_7$.½H$_2$O; Calc'd: C, 63.90; H, 8.30; N, 7.22; Found: C, 63.81; H, 8.17; N, 6.93. % I=86%

EXAMPLE 11

Beta-[[2-[[2-[1,3-dihydro-1-oxo-2H-isoindol-2-yl]-1-oxo-3-phenylpropyl]amino]-oxo-pentyl]amino]-alphahydroxycyclohexanebutanoic acid 1-methylethyl ester TFA-ACHBA-O$^i$Pr (0.64 mmol) was coupled to Boc-norvaline utilizing the procedure of Example 1, second paragraph, to yield after flash chromatography (5-15% Et$_2$O/CH$_2$Cl$_2$; SiO$_2$ gel), 0.16 g (57% yield) of isopropyl α-N-(t-butyloxycarbonyl)norvalyl-3-amino-4-cyclohexyl-2-hydroxybutanoate.

$^1$H-NMR (CDCl$_3$, 200 MHz) δ6.03 and 6.20 (2d, 1H), 4.88-5.10 (m, 2H), 4.48 (m, 1H), 3.89-4.42 (m, 2H), 3.15 (d, 1H), 0.81-1.89 (m, 35H)

FAB-MS (M+H)+ =443.

The product from the preceding paragraph (0.36 mmol) was deprotected utilizing the procedure presented in paragraph 1 of Example 1 to yield the TFA salt [FAB-MS (M+H)+ =343 (free base)] which was coupled to N-(1-oxo-2H-isoindol-2-yl)-Phe-OH utilizing the procedure of Example 1 to yield, after flash chromatography (1:10:10 v/v/v MeOH/Et$_2$O/CH$_2$Cl$_2$; SiO$_2$ gel), 0.15 g (71% yield) of the title compound as a white solid. HPLC indicated a diastereomeric ratio of 4.8:1.

$^1$H-NMR (CDCl$_3$, 200 MHz) δ7.83 (d, 1H), 7.53 (t, 1H), 7.45 (t, 1H), 7.39 (d, 1H), 7.16-7.31 (m, 5H), 6.89 and 7.09 (2d, 1H), 6.07 and 6.18 (2d, 1H), 4.98-5.08 (m, 2H), 4.34-4.45 (m, 3H), 4.17 (m, 1H), 4.06 (bs, 1H), 3.20-3.43 (m, 3H), 0.75-1.84 (m, 26H)

FAB-MS (M+H)+ =606.

Elemental analysis for C$_{35}$H$_{47}$N$_3$O$_6$; Calc'd: C, 69.40; H, 7.82; N, 6.94; Found: C, 69.07; H, 7.89; N, 6.76. % I=99%

EXAMPLE 12

Beta-[[2-[[2-[1,3-dihydro-1-oxo-2H-isoindol-2-yl]-1-oxo-3-phenylpropyl]amino]-1-oxo-hexyl]amino]-alphahydroxycyclohexanebutanoic acid 1-methylethyl ester TFA-ACHBA-O$^i$Pr (0.59 mmol) was coupled to Boc-norleucine utilizing the procedure of Example 1, paragraph 2, to yield, after flash chromatography (5% Et$_2$O/CH$_2$Cl$_2$; SiO$_2$ gel) 0.148 g (55% yield) of isopropyl $\alpha$N-(t-butyloxycarbonyl)norleucyl-3-amino-4-cyclohexyl-2-hydroxybutanoate as a white solid.

$^1$H-NMR (CDCl$_3$, 200 MHz) $\delta$6.09 and 6.25 (2d, 1H), 4.91–5.18 (m, 2H), 4.47 (m, 1H), 3.88–4.25 (m, 3H), 3.22 (bs, 1H), 0.86–1.90 (m, 37H)

FAB-MS (M+H)$^+$ =457.

The product from the preceding paragraph (0.32 mmol) was deprotected utilizing the procedure presented in paragraph 1 of Example 1 to yield the TFA salt [FAB-MS (M+H)$^+$ =357 (free base)] which was coupled directly to N-(1-oxo-2H-isoindol-2-yl)-Phe-OH utilizing the procedure of Example 1, paragraph 2, to yield, after flash chromatography (1:20:140 v/v/v MeOH/Et$_2$O/CH$_2$Cl$_2$; SiO$_2$ gel), 0.084 g (42% yield) of the title compound as a white solid. HPLC indicates a diastereomeric ratio of 15.7:1.

$^1$H-NMR (CDCl$_3$, 400 MHz) $\delta$7.83 (dd, 1H), 7.17–7.53 (m, 8H), 6.83 (d, 1H), 6.04 (d, 1H), 4.98–5.09 (m, 2H), 4.38–4.45 (m, 3H), 4.16 (M, 1H), 4.04 (M, 1H), 3.08–3.40 (M, 3H), 0.64–1.86 (m, 28H), 0.66 (t, 3H)

FAB-MS (M+H)$^+$ =620.

Elemental analysis for C$_{36}$H$_{49}$N$_3$O$_6$.½H$_2$O; Calc'd: C, 68.76; H, 8.01; N, 6.68; Found: C, 68.92; H, 7.82; N, 6.45. % I=99%

EXAMPLE 13

Beta-[[2-[[2-[1,3-dihydro-1-oxo-2H-benzisoquinolin-2-yl]-1-oxo-3-phenylpropyl]amino]-4-methyl-1-oxo-pentyl]amino]-alphahydroxycyclohexanebutanoic acid 1-methylethyl ester N-(1,3-Dihydro-1-oxo-2H-benzisoquinolin-2-yl)-L-phenylalanine was prepared from L-phenylalanine and 8-formyl-1-napthoic acid methyl ester (Matsubayashi et al., Japan, Kokai 76, 82, 246) (2.37 mmol) utilizing the procedure illustrated in the first paragraph of Example 2, supra. Flash chromatography (1:10:80 v/v/v CH$_3$CO$_2$H/Et$_2$O/CH$_2$Cl$_2$; SiO$_2$ gel) provided pure product (0.170 g) in 22% yield.

$^1$H-NMR (CDCl$_3$, 200 MHz) $\delta$8.32 (d, 1H), 7.96 (d, 1H), 7.76 (d, 1H), 7.54 (t, 1H), 7.45 (t, 1H), 7.21 (m, 6H), 5.04 (dd, 1H), 4.79 (dd, 2H), 3.53 (m, 2H).

EI-MS m/e=331.

The product of the preceding paragraph (0.51 mmol) was coupled to TFA-Leu-ACHBA-O$^i$Pr utilizing the procedure presented in paragraph 2 of Example 1 to yield, after flash chromatography (35% EtOAc/hexane; SiO$_2$gel), 0.218 g (63% yield) of the title compound as an off-white solid. HPLC indicated a diastereomeric ratio of 4.25:1.

$^1$H-NMR (CDCl$_3$, 400 MHz) $\delta$8.59 and 8.29 (2d, 1H), 8.23 and 7.95 (2d, 1H), 7.75 (d, 1H), 7.57 (t, 1H), 7.47 (t, 1H), 7.13–7.36 (m, 6H), 6.70 and 6.86 (2d, 1H), 6.27 and 6.38 (2d, 1H), 5.50 (m, 1H), 4.82–5.09 (m, 3H), 4:15–4.45 (m, 3H), 4.04 (d, 1H), 3.28–3.50 (m, 2H), 0.60–1.84 (m, 26H)

FAB-MS (M+H)$^+$ =670.

Elemental analysis for C$_{40}$H$_{51}$N$_3$O$_6$.¾H$_2$O; Calc'd: C, 70.30; H, 7.74; N, 6.14; Found: C, 70.27; H, 7.42; N, 6.11. % I=92%

EXAMPLE 14

Beta-[[2-[[2-[2-oxo-1-pyrrolidinyl]-1-oxo-3-phenylpropyl]amino]-4-methyl-1-oxo-pentyl]amino]-alpha-hydroxycyclohexanebutanoic acid 1-methylethyl ester To a slurry of L-phenylalanine methyl ester hydrochloride (4.64 mmol) in CH$_3$CN (10 mL) was added K$_2$CO$_3$ (16.2 mmol) and ethyl-4-bromobutyrate (5.1 mmol). The reaction mixture was stirred overnight at room temperature. Another 0.2 mL of ethyl 4-bromobutyrate was added, the reaction mixture was stirred for 3 days at 50° C. and then quenched with H$_2$O. The aqueous layer was extracted with EtOAc (3×50 mL). The combined organic layers were then extracted with 0.5 N HCl (3×50 ml). The pH of the aqueous layer was raised to about 8 with solid NaHCO$_3$, and this layer was then extracted with EtOAc (3×50 mL). The combined organic layers were washed with brine, dried over MgSO$_4$, filtered, concentrated, and flash chromatographed (5–10% Et$_2$O/CH$_2$Cl$_2$; SiO$_2$ gel) to yield 0.577 g of amine diester as a pale yellow oil [FAB-MS (M+H)$^+$ =294]. This compound was dissolved in toluene (10 mL), refluxed for 46 hours, diluted with Et$_2$O, washed with 0.5 N HCl and brine, dried over MgSO$_4$, filtered, and concentrated to provide 0.322 g (75% yield) of N-(2-oxo-1-pyrrolidinyl)-L-phenylalanine methyl ester as a pale yellow oil.

$^1$H-NMR (CDCl$_3$, 200 MHz) $\delta$7.25 (m, 5H), 5.10 (dd, 1H), 3.72 (s, 3H), 3.29–3.45 (m, 3H), 2.99 (dd, 1H), 1.85–2.35 (m, 4H).

FAB-MS (M+H)$^+$ =284.

The product of the preceding paragraph (1.3 mmol) was deprotected utilizing the procedure of the third step in Example 2 to yield 0.286 g of the acid which was directly coupled to TFA-Leu-ACHBA-O$^i$Pr (0.56 mmol) utilizing the procedure of Example 1, paragraph 2, to yield, after flash chromatography (1:20:80 v/v/v CH$_3$OH/EtOAc/CH$_2$Cl$_2$; SiO$_2$ gel), 0.16 g (50% yield) of the title compound as a white solid. HPLC indicated a diastereomeric ratio of 3.8:1.

$^1$H-NMR (CDCl$_3$, 400 MHz) $\delta$7.20–7.34 (m, 5H), 6.62 and 6.82 (2d, 1H), 6.17 and 6.26 (2d, 1H), 5.03 and 5.10 (m, 1H), 4.75 and 4.81 (2dd, 1H), 4.44 (dq, 1H), 4.23 (m, 1H), 4.07 (bs, 1H), 3.09–3.44 (m, 3H), 2.31 (m, 2H), 1.90 (m, 2H), 0.86–1.74 (m, 30H)

FAB-MS (M+H)$^+$ =572.

Elemental analysis for C$_{32}$H$_{49}$N$_3$O$_6$.½H$_2$O; Calc'd: C, 66.18; H, 8.68; N, 7.23; Found: C, 66.41; H, 8.49; N, 7.11. % I=93%

EXAMPLE 15

Beta-[[2-[[2-[5-oxo-5H-imidazo[1,2-a]imidazol-6(7H)-yl]-1-oxo-3-phenylpropyl]amino]-4-methyl-1-oxo-pentyl]amino]-alphahydroxycyclohexanebutanoic acid 1-methylethyl ester N-(2-methylimidazolyl)-L-phenylalanine methyl ester was prepared from L-phenylalanine methyl ester hydrochloride (3.30 mmol) and 2-formyl-imidazole (3.63 mmol) utilizing the procedure of Example 9, first paragraph, to yield, after flash chromatography (3:50:50 v/v/v CH$_3$OH/EtOAc/CH$_2$Cl$_2$; SiO$_2$ gel), 0.55 g (65% yield) of pure product.

$^1$H-NMR (CDCl$_3$, 200 MHz) δ7.25 (m, 5H), 6.79 (s, 2H), 3.86 (q, 2H), 3.73 (s, 3H), 3.26 (q, 1H), 2.75 and 3.08 (2 dd, 2H).

EI-MS m/e=259.

The product of the preceding paragraph (2.12 mmol) was cyclized utilizing the procedure of Example 9, second paragraph, to yield, after flash chromatography (30% EtOAc/CH$_2$Cl$_2$; SiO$_2$ gel), 0.51 g (84% yield) of N-(5-oxo-5H-imidazo[1,2-a]-imidazol-6(7H)-yl)-L-phenylalanine methyl ester as a yellow oil.

$^1$H-NMR (CDCl$_3$, 200 MHz) δ7.23 (m, 5H), 6.99 and 7.14 (2s, 2H), 5.15 (dd, 1H), 4.43 (dd, 2H), 3.78 (s, 3H), 3.11 and 3.50 (2 dd, 2H)

EI-MS m/e=285.

The product of the preceding paragraph (0.60 mmol) was deprotected utilizing the procedure of the third step in Example 2 to yield 0.075 g (46%) of the acid which was directly coupled to TFA-Leu-ACHBA-O$^i$Pr (0.34 mmol) utilizing the procedure of Example 1, second paragraph, to yield, after flash chromatography (1-3:20:80 v/v/v CH$_3$OH/EtOAC/CH$_2$Cl$_2$; SiO$_2$ gel), 0.101 g (49% yield) of the title compound as a white solid. HPLC indicated a mixture of four diastereomers in a ratio of 5:3:1:1.

$^1$H-NMR (CDCl$_3$, 400 MHz) δ7.13-7.33 (m, 7H), 6.42 and 6.50 (2d, 1H), 5.99-6.16 (m, 1H), 4.81-5.13 (m, 2H), 3.99-4.62 (m, 4H), 3.08-3.37 (m, 2H), 0.71-1.87 (m, 28H)

FAB-MS (M+H)$^+$=610.

Elemental analysis for C$_{33}$H$_{47}$N$_5$O$_6$·$\frac{3}{4}$H$_2$O; Calc'd: C, 63.59; H, 7.84; N, 11.23; Found: C, 63.59; H, 8.08; N, 10.92.

% I=96%

EXAMPLE 16

Beta-[[2-[[2-[(7aS)-tetrahydro-3-oxo-1H-pyrrolo[1,2-c]imidazol-2(3H)-yl]-1-oxo-3-phenylpropyl]amino]-4-methyl-1-oxo-pentyl]amino]-alphahydroxycyclohexanebutanoic acid 1-methylethyl ester N-(N-t-butyloxycarbonyl)-5H-pyrrololyl-2-methyl)-L-phenylalanine methyl ester was prepared from L-phenylalanine methyl ester hydrochloride (4.13 mmol) and Boc-prolinal [4.13 mmol, Hamada and Shiori, Chem. Pharm. Bull. (1982) 30, 1921] utilizing the procedure of the first paragraph of Example 9 to yield, after flash chromatography (15-25% Et$_2$O/CH$_2$Cl$_2$; SiO$_2$ gel), 0.588 g (40% yield) of pure product.

$^1$H-NMR (CDCl$_3$, 200 MHz) δ7.22 (m, 5H), 3.79 (bs, 1H), 3.64 (s, 3H), 3.50 (bs, 1H), 3.28 (bs, 2H), 2.91 (m, 2H), 2.59 (m, 3H), 1.76 (m, 4H), 1.44 (s, 9H).

FAB-MS (M+H)$^+$=385.

The product of the preceding paragraph (1.19 mmol) was deprotected utilizing the procedure presented in paragraph 1 of Example 8 to give the free amine (0.253 g, 81%), which was used directly in the cyclization reaction. To the crude amine in THF (25 mL) was added 1,1-carbonyl-diimidazole (1.25 mmol). The reaction mixture was stirred overnight at room temperature, quenched with 0.5 N HCl, and extracted with EtOAc (3×80 mL). The combined organic layers were washed with 0.5 N HCl, saturated bicarbonate, brine, dried over MgSO$_4$, filtered, concentrated, and flash chromatographed (first in 100% CH$_2$Cl$_2$, then 100% Et$_2$O; SiO$_2$ gel) to yield 0.151 g (55%) of N-((7aS)-tetrahydro-3-oxo-1H-pyrrolo[1,2-c]imidazol-2(3H)-yl)-L-phenylalanine methyl ester.

$^1$H-NMR (CDCl$_3$, 200 MHz) δ7.24 (m, 5H), 4.90 (dd, 1H), 3.71 (s, 3H), 3.29-3.61 (m, 5H), 2.99 (m, 2H), 1.69-1.93, (m, 3H), 1.41 (m, 1H).

FAB-MS (M+H)$^+$=289

The product of the preceding paragraph (0.52 mmol) was deprotected utilizing the procedure of the third paragraph of Example 2 to yield 0.137 g (95%) of the acid which was directly coupled to TFA-Leu-ACHBA-O$^i$Pr (0.46 mmol) utilizing the procedure of Example 1, paragraph 2, to yield, after flash chromatography (1:9:90 v/v/v CH$_3$OH/Et$_2$O/CH$_2$Cl$_2$; SiO$_2$ gel), 0.157 g (56% yield) of the title compound as a white solid. HPLC indicated a diastereomeric ratio of 3.2:1.

$^1$H-NMR (CDCl$_3$, 200 MHz) δ7.19-7.31 (m, 5H), 6.90 and 6.99 (2d, 1H), 6.12 and 6.24 (2d, 1H), 4.93-5.11 (m, 1H), 4.04-4.61 (m, 5H), 3.51-3.65 (m, 3H), 3.34 (d, 1H), 2.99-3.30 (m, 3H), 0.71-1.91 (m, 32H)

FAB-MS (M+H)$^+$=613

Elemental analysis for C$_{34}$H$_{52}$N$_4$O$_6$·1.5 H$_2$O; Calc'd: C, 63.82; H, 8.66; N, 8.76; Found: C, 63.49; H, 8.70; N, 9.17.

% I=91%

What is claimed is:

1. A compound of the formula:

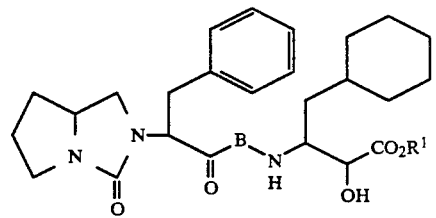

in which

B is His, Leu, Ile, Nva, Nle, Ala or Val; and

R$^1$ is hydrogen, alkyl of 1 to 6 carbon atoms, phenyl or phenylalkyl in which the alkyl group has 1 to 6 carbon atoms;

or a pharmaceutically acceptable salt thereof.

2. The compound of claim 1 which is beta-[[2-[[2-[(7aS)-tetrahydro-3-oxo-1H-pyrrolo[1,2-c]imidazol-2(3H)-yl]-1-oxo-3-phenylpropyl]amino]-4-methyl-1-oxo-pentyl]amino]-alpha-hydroxycyclohexanebutanoic acid 1-methylethyl ester, or a pharmaceutically acceptable salt thereof.

* * * * *